US012569531B2

(12) United States Patent
Wang et al.

(10) Patent No.: US 12,569,531 B2
(45) Date of Patent: Mar. 10, 2026

(54) TRADITIONAL CHINESE HERBAL COMPOSITION FOR TREATING PULMONARY NODULE, PREPARATION METHOD THEREOF, AND HONEYED PILL

(71) Applicant: Changchun University of Traditional Chinese Medicine

(72) Inventors: Tan Wang, Changchun (CN); Shaodan Hu, Changchun (CN); Mengzhu Chen, Changchun (CN); Yujiao Liu, Changchun (CN); Yannan Xu, Changchun (CN); Wenlong Qi, Changchun (CN); Keju Wang, Changchun (CN); Ziyuan Wang, Changchun (CN)

(73) Assignee: Changchun University of Traditional Chinese Medicine, Changchun (CN)

( * ) Notice: Subject to any disclaimer, the term of this patent is extended or adjusted under 35 U.S.C. 154(b) by 662 days.

(21) Appl. No.: 18/047,499

(22) Filed: Oct. 18, 2022

(65) Prior Publication Data

US 2024/0131106 A1 Apr. 25, 2024

(51) Int. Cl.
| | |
|---|---|
| *A61K 36/725* | (2006.01) |
| *A61K 9/00* | (2006.01) |
| *A61K 36/258* | (2006.01) |
| *A61K 36/328* | (2006.01) |
| *A61K 36/428* | (2006.01) |
| *A61K 36/65* | (2006.01) |
| *A61K 36/804* | (2006.01) |
| *A61P 11/00* | (2006.01) |

(52) U.S. Cl.
CPC .......... *A61K 36/725* (2013.01); *A61K 9/0056* (2013.01); *A61K 36/258* (2013.01); *A61K 36/328* (2013.01); *A61K 36/428* (2013.01); *A61K 36/65* (2013.01); *A61K 36/804* (2013.01); *A61P 11/00* (2018.01)

(58) Field of Classification Search
CPC .. A61K 36/725; A61K 9/0056; A61K 36/258; A61K 36/328; A61K 36/428; A61K 36/65; A61K 36/804; A61K 35/58; A61K 35/644; A61K 36/076; A61K 36/73; A61K 36/8994; A61P 11/00
See application file for complete search history.

(56) References Cited

U.S. PATENT DOCUMENTS 7,300,676 B2 * 11/2007 Chen ...................... A61K 36/00
424/725

* cited by examiner

*Primary Examiner* — Aaron J Kosar

(57) ABSTRACT

Provided is a traditional Chinese herbal composition for treating pulmonary nodules, a preparation method thereof, and a honeyed pill. The composition comprises: 30 parts by weight of Ziziphi Spinosae Semen, 20-30 parts by weight of Rehmaniae Radix, 30 parts by weight of Trichosanthis Radix, 40-50 parts by weight of Paeoniae Radix Alba, 30 parts by weight of Coicis Semen Preparata, 20 parts by weight of Ginseng Radix et Rhizoma, 10 parts by weight of Olibanum, 10 parts by weight of Myrrha, 20-30 parts by weight of Testudinis Carapax et Plastrum Preparata Cum Aceto, 20-30 parts by weight of Trionycis Carapax Preparata Cum Aceto, 30 parts by weight of Agrimoniae Herba, 10-20 parts by weight of Alpiniae Oxyphyllae Fructus, 5 parts by weight of Toosendan Fructus, 20 parts by weight of Poria, 10 parts by weight of Platycodonis Radix, and 10 parts by weight of Polygalae Radix.

9 Claims, No Drawings

TRADITIONAL CHINESE HERBAL COMPOSITION FOR TREATING PULMONARY NODULE, PREPARATION METHOD THEREOF, AND HONEYED PILL

TECHNICAL FIELD

The present disclosure relates to the technical field of traditional Chinese medicine (TCM), in particular to a traditional Chinese herbal composition for treating pulmonary nodules, a preparation method thereof, and a honeyed pill.

BACKGROUND ART

With the development of imaging (CT) and the popularization of health check-up, more and more pulmonary nodules are found in the clinical setting. Pulmonary nodules are focal, quasi-circular, hyperdense, solid or subsolid lung opacities with a diameter of ≤3 cm, which may be solitary or multiple, without pulmonary atelectasis, hilar lymphadenophathy, and pleural effusion. Nodules grown in the lungs may be either benign or malignant. Benign lesions include inflammatory pseudotumor, hamartoma, and tuberculoma; malignant lesions may be pulmonary carcinoma or intrapulmonary metastasis. Most of solitary pulmonary nodules show no obvious symptoms, and reveal well-circumscribed and hyperdense soft tissue opacities with a diameter of ≤3 cm and surrounded by aerated lung tissues. Multiple pulmonary nodules usually manifest as a single pulmonary nodule with one or more small nodules. It is generally believed that more than 10 diffuse pulmonary nodules are mostly caused by metastases of malignant tumors or benign lesions (inflammatory diseases caused by infectious or noninfectious factors); local lesions with a diameter of >3 cm are known as pulmonary masses, and there is a relatively greater chance for pulmonary carcinoma. Herein, the diagnosis of small pulmonary nodules is significantly improved, and partial small pulmonary nodules are early signs of primary pulmonary carcinoma. Therefore, early intervention treatment is particularly important and has positive significance for the prognoses of patients. It is believed in Western medicine that asymptomatic pulmonary nodules do not require treatment, but should be reviewed regularly at an interval of 1, 3, 6, or 12 months; there is no drug intervention method in the monitoring period. In case of enlarged lesions during the monitoring, it should be considered that malignancies should be treated with surgical resection and postoperative chemoradiotherapy. There is no consensus in TCM so far. Discussions on the etiology, pathogenesis, therapeutic principle, and effective prescriptions of pulmonary nodules in TCM are almost blank in the field of TCM.

SUMMARY

In view of this, an objective of the present disclosure is to provide a traditional Chinese herbal composition for treating pulmonary nodules, a preparation method thereof, and a honeyed pill. The traditional Chinese herbal composition provided by the present disclosure can effectively improve pulmonary nodules and a plurality of clinical symptoms caused thereby, with significant efficacy and without side effect.

To achieve the above objective, the present disclosure provides the following technical solutions:

Disclosed herein is a traditional Chinese herbal composition for treating pulmonary nodules prepared from raw materials comprising the following in relative parts by weight: 30 parts by weight of Ziziphi Spinosae Semen, 20-30 parts by weight of Rehmanniae Radix, 30 parts by weight of Trichosanthis Radix, 40-50 parts by weight of Paeoniae Radix Alba, 30 parts by weight of Coicis Semen Preparata, 20 parts by weight of Ginseng Radix et Rhizoma, 10 parts by weight of Olibanum, 10 parts by weight of Myrrha, 20-30 parts by weight of Testudinis Carapax et Plastrum Preparata Cum Aceto, 20-30 parts by weight of Trionycis Carapax Preparata Cum Aceto, 30 parts by weight of Agrimoniae Herba, 10-20 parts by weight of Alpiniae Oxyphyllae Fructus, 5 parts by weight of Toosendan Fructus, 20 parts by weight of Poria, 10 parts by weight of Platycodonis Radix, and 10 parts by weight of Polygalae Radix.

The present disclosure provides a preparation method of the traditional Chinese herbal composition according to the above solution, including the following steps:

Step 1, soaking the Ziziphi Spinosae Semen, the Rehmanniae Radix, the Trichosanthis Radix, the Paeoniae Radix Alba, the Coicis Semen Preparata, the Ginseng Radix et Rhizoma, the Olibanum, the Myrrha, the Testudinis Carapax et Plastrum Preparata Cum Aceto, the Trionycis Carapax Preparata Cum Aceto, the Agrimoniae Herba, the Alpiniae Oxyphyllae Fructus, the Toosendan Fructus, the Poria, the Platycodonis Radix, and the Polygalae Radix in water;

Step 2, conducting a first decoction on medicinal materials soaked in step 1 to obtain a first decoction and first dregs;

Step 3, mixing the first dregs obtained in step 2 with water for a second decoction to obtain a second decoction and second dregs;

Step 4, mixing the second dregs obtained in step 3 with water for a third decoction to obtain a third decoction and third dregs; and Step 5, mixing the decoctions obtained in steps 2, 3, and 4 to obtain the traditional Chinese herbal composition.

Preferably, the soaking in step 1 may be conducted for about 15-25 min.

Preferably, an amount of the water in step 1, 3, or 4 may be each independently about 2-3 cm above the surface of the medicinal materials, that of the first dregs, or that of the second dregs.

Preferably, the first decoction, the second decoction, and the third decoction may be each independently implemented by boiling a liquor and decocting the liquor.

Preferably, the decocting may each independently last for about 20-40 min during the first decoction and the second decoction.

Preferably, the decocting may last for about 15-25 min during the third decoction.

The present disclosure further provides a honeyed pill for treating pulmonary nodules, including the raw materials of the traditional Chinese herbal composition according to the above solution and honey; a total mass of the raw materials of the traditional Chinese herbal composition and a mass of the honey are in a ratio of 1:(1.2-1.5).

Preferably, the traditional Chinese herbal composition may be in the pharmaceutical dosage form of a tablet, a granule, a capsule, and an oral liquid preparation.

In the present disclosure, the Ziziphi Spinosae Semen nourishes the heart and quiets the spirit, conciliates five internal organs, and restores the function of the heart controlling mental activities. The Ginseng Radix et Rhizoma powerfully reinforces original qi, and induces tranquilization; if compatible with the Alpiniae Oxyphyllae Fructus, the action of inducing tranquilization and sharpening the wits is reinforced, heart yang is raised up, free coursing of liver qi is normally realized, evil qi is eliminated, binding depression is dissipated, and functioning of qi is diffused. The Rehmanniae Radix nourishes yin and engenders liquid; if compatible with the Paeoniae Radix Alba, actions of emolliating the liver, retaining yin with astringent and relieving pain can be reinforced, so that nourishing is replaced with draining and excessive exuberance of liver yang is suppressed. The Toosendan Fructus courses the liver and moves qi, conforms to the regulatory nature of liver-wood, helps calm the ministerial fire, and accelerates the disappearance of phlegm-rheum and water-damp; the Trichosanthis Radix nourishes yin and represses the liver, engenders liquid, and nourishes the heart; the Coicis Semen Preparata disinhibits water and fortifies the spleen. Combi-nation of these three herbs can disperse swelling, while reinforcing the transport and distribution of qi-blood-body fluid and enhancing the function of qi transformation. The Olibanum and the Myrrha can promote blood circulation to arrest pain, disperse swelling and engender flesh; the Testu-dinis Carapax et Plastrum Preparata Cum Aceto nourishes yin and suppresses yang, nourishes blood, and tonifies the heart; the Trionycis Carapax Preparata Cum Aceto nourishes yin and suppresses yang, and softens hardness to dissipate stagnation. Combination of these four herbs can nourish liver yin and suppresses liver yang to reinforce the function of eliminating stagnation and dispersing swelling and nour-ish the heart. The Agrimoniae Herba arrests bleeding, treats scrofula, has an action of dispersing accumulations, and blocks the growth of accumulations herein. The Poria quiets the heart, induces tranquilization, tonifies the heart and the spleen, and assists the Ziziphi Spinosae Semen to regulate and conserve the heart spirit herein. The Platycodonis Radix diffuses the lungs, disperses welling-abscesses, and con-ducts medicinals upward, serving as a medicinal guide. The Polygalae Radix assists the Ziziphi Spinosae Semen to induce tranquilization and sharpen the wits. Herein, the Ziziphi Spinosae Semen serves as a sovereign drug, the Ginseng Radix et Rhizoma, the Rehmanniae Radix, and the Paeoniae Radix Alba serve as ministerial drugs, the Coicis Semen Preparata, the Trichosanthis Radix, the Testudinis Carapax et Plastrum Preparata Cum Aceto, the Trionycis Carapax Preparata Cum Aceto, the Olibanum, the Myrrha, the Agrimoniae Herba, the Alpiniae Oxyphyllae Fructus, the Toosendan Fructus, the Poria, and the Polygalae Radix serve as adjuvant drugs, and the Platycodonis Radix serves as an envoy drug, jointly playing roles in nourishing yin to elimi-nate foreign bodies and breaking masses to eliminate stag-nation.

The traditional Chinese herbal composition by the present disclosure and the honeyed pill prepared therewith can effectively improve pulmonary nodules and a plurality of clinical symptoms caused thereby, with significant efficacy and without side effect.

Also disclosed are methods of treating pulmonary nodules comprising administering to a subject a traditional Chinese herbal composition according to the present disclosure. Also disclosed are methods of treating pulmonary nodules com-prising administering to a subject a honeyed pill according to the present disclosure.

DETAILED DESCRIPTION OF THE EMBODIMENTS

The present disclosure is not to be limited in terms of the particular embodiments described in this application, which are intended as illustrations of various aspects. Many modi-fications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the termi-nology used herein is for the purpose of describing particular embodiments only and is not intended to be limiting.

As used in this document, the singular forms "a," "an," and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior inven-tion. As used in this document, the term "comprising" means "including, but not limited to."

While various compositions, methods, and devices are described in terms of "comprising" various components or steps (interpreted as meaning "including, but not limited to"), the compositions, methods, and devices can also "con-sist essentially of" or "consist of" the various components and steps, and such terminology should be interpreted as defining essentially closed-member groups.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (for example, bodies of the appended claims) are generally intended as "open" terms (for example, the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (for example, "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

All percentages, parts and ratios are based upon the total weight of the compositions and all measurements made are at about 25° C., unless otherwise specified.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

The term "about," as used herein, refers to variations in a numerical quantity that can occur, for example, through measuring or handling procedures in the real world; through inadvertent error in these procedures; through differences in the manufacture, source, or purity of compositions or reagents; and the like. Typically, the term "about" as used herein means greater or lesser than the value or range of values stated by $\frac{1}{10}$ of the stated values, e.g., ±10%. The term "about" also refers to variations that would be recognized by one skilled in the art as being equivalent so long as such variations do not encompass known values practiced by the prior art. Each value or range of values preceded by the term "about" is also intended to encompass the embodiment of the stated absolute value or range of values. Whether or not modified by the term "about," quantitative values recited in the present disclosure include equivalents to the recited values, e.g., variations in the numerical quantity of such values that can occur, but would be recognized to be equivalents by a person skilled in the art. Where the context of the disclosure indicates otherwise, or is inconsistent with such an interpretation, the above-stated interpretation may be modified as would be readily apparent to a person skilled in the art. For example, in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

Where a range of values is provided, it is intended that each intervening value between the upper and lower limit of that range and any other stated or intervening value in that stated range is encompassed within the disclosure. For example, if a range of 1 μm to 8 μm is stated, it is intended that 2 μm, 3 μm, 4 μm, 5 μm, 6 μm, and 7 μm are also explicitly disclosed, as well as the range of values greater than or equal to 1 μm and the range of values less than or equal to 8 μm.

The term "patient" and "subject" are interchangeable and may be taken to mean any living organism which may be treated with compounds of the present invention. As such, the terms "patient" and "subject" may include, but is not limited to, any non-human mammal, primate or human. In some embodiments, the "patient" or "subject" is a mammal, such as mice, rats, other rodents, rabbits, dogs, cats, swine, cattle, sheep, horses, primates, or humans. In some embodiments, the patient or subject is an adult, child or infant. In some embodiments, the patient or subject is a human. In yet other embodiments, the patient or subject with pulmonary nodules.

The present disclosure provides a traditional Chinese herbal composition for treating pulmonary nodules. The traditional Chinese herbal composition is prepared with the following raw materials: 30 parts by weight of Ziziphi Spinosae Semen, 20-30 parts by weight of Rehmanniae Radix, 30 parts by weight of Trichosanthis Radix, 40-50 parts by weight of Paeoniae Radix Alba, 30 parts by weight of Coicis Semen Preparata, 20 parts by weight of Ginseng Radix et Rhizoma, 10 parts by weight of Olibanum, 10 parts by weight of Myrrha, 20-30 parts by weight of Testudinis Carapax et Plastrum Preparata Cum Aceto, 20-30 parts by weight of Trionycis Carapax Preparata Cum Aceto, 30 parts by weight of Agrimoniae Herba, 10-20 parts by weight of Alpiniae Oxyphyllae Fructus, 5 parts by weight of Toosendan Fructus, 20 parts by weight of Poria, 10 parts by weight of Platycodonis Radix, and 10 parts by weight of Polygalae Radix.

Disclosed herein is a traditional Chinese herbal composition for treating pulmonary nodules prepared from raw materials comprising the following in relative parts by weight: 30 parts by weight of Ziziphi Spinosae Semen, 20-30 parts by weight of Rehmanniae Radix, 30 parts by weight of Trichosanthis Radix, 40-50 parts by weight of Paeoniae Radix Alba, 30 parts by weight of Coicis Semen Preparata, 20 parts by weight of Ginseng Radix et Rhizoma, 10 parts by weight of Olibanum, 10 parts by weight of Myrrha, 20-30 parts by weight of Testudinis Carapax et Plastrum Preparata Cum Aceto, 20-30 parts by weight of Trionycis Carapax Preparata Cum Aceto, 30 parts by weight of Agrimoniae Herba, 10-20 parts by weight of Alpiniae Oxyphyllae Fructus, 5 parts by weight of Toosendan Fructus, 20 parts by weight of Poria, 10 parts by weight of Platycodonis Radix, and 10 parts by weight of Polygalae Radix.

Disclosed herein is a traditional Chinese herbal composition for treating pulmonary nodules prepared from raw materials comprising the following in relative parts by weight: about 30 parts by weight of Ziziphi Spinosae Semen, about 20-30 parts by weight of Rehmanniae Radix, about 30 parts by weight of Trichosanthis Radix, about 40-50 parts by weight of Paeoniae Radix Alba, about 30 parts by weight of Coicis Semen Preparata, about 20 parts by weight of Ginseng Radix et Rhizoma, about 10 parts by weight of Olibanum, about 10 parts by weight of Myrrha, about 20-30 parts by weight of Testudinis Carapax et Plastrum Preparata Cum Aceto, about 20-30 parts by weight of Trionycis Carapax Preparata Cum Aceto, about 30 parts by weight of Agrimoniae Herba, about 10-20 parts by weight of Alpiniae Oxyphyllae Fructus, about 5 parts by weight of Toosendan Fructus, about 20 parts by weight of Poria, about 10 parts by weight of Platycodonis Radix, and about 10 parts by weight of Polygalae Radix.

Disclosed herein is a traditional Chinese herbal composition for treating pulmonary nodules prepared from raw materials comprising the following in relative parts by weight: of 30 parts by weight of Ziziphi Spinosae Semen, 20-30 parts by weight of Rehmanniae Radix, 30 parts by weight of Trichosanthis Radix, 40-50 parts by weight of Paeoniae Radix Alba, 30 parts by weight of Coicis Semen Preparata, 20 parts by weight of Ginseng Radix et Rhizoma, 10 parts by weight of Olibanum, 10 parts by weight of Myrrha, 20-30 parts by weight of Testudinis Carapax et Plastrum Preparata Cum Aceto, 20-30 parts by weight of Trionycis Carapax Preparata Cum Aceto, 30 parts by weight of Agrimoniae Herba, 10-20 parts by weight of Alpiniae Oxyphyllae Fructus, 5 parts by weight of Toosendan Fructus, 20 parts by weight of Poria, 10 parts by weight of Platycodonis Radix, and 10 parts by weight of Polygalae Radix.

Disclosed herein is a traditional Chinese herbal composition for treating pulmonary nodules prepared from raw materials comprising the following in relative parts by weight: about 30 parts by weight of Ziziphi Spinosae Semen, about 20-30 parts by weight of Rehmanniae Radix, about 30 parts by weight of Trichosanthis Radix, about 40-50 parts by weight of Paeoniae Radix Alba, about 30 parts by weight of Coicis Semen Preparata, about 20 parts by weight of Ginseng Radix et Rhizoma, about 10 parts by weight of Olibanum, about 10 parts by weight of Myrrha, about 20-30 parts by weight of Testudinis Carapax et Plastrum Preparata Cum Aceto, about 20-30 parts by weight of Trionycis Carapax Preparata Cum Aceto, about 30 parts by weight of Agrimoniae Herba, about 10-20 parts by weight of Alpiniae Oxyphyllae Fructus, about 5 parts by weight of Toosendan Fructus, about 20 parts by weight of Poria, about 10 parts by weight of Platycodonis Radix, and about 10 parts by weight of Polygalae Radix.

The terms "administer," "administering" or "administration" as used herein refer to either directly administering a compound, product or a composition to a subject. In some embodiments, administer," "administering" or "administration" as used herein refers to topically administering a compound, product or composition described herein to the skin.

The term "treat," "treated," or "treating" as used herein refers to both therapeutic treatment and prophylactic or preventative measures, wherein the object is to reduce the frequency of, or delay the onset of, symptoms of a medical condition, enhance the texture, appearance, color, sensation, or hydration of the intended tissue treatment area of the tissue surface in a subject relative to a subject not receiving the compound or composition, or to otherwise obtain beneficial or desired clinical results. For the purposes of this invention, beneficial or desired clinical results include, but are not limited to, reversal, reduction, or alleviation of symptoms of a condition; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment includes eliciting a clinically significant response without excessive levels of side effects. Treatment also includes prolonging survival as compared to expected survival if not receiving treatment.

By hereby reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by hereby reserving the right to proviso out or exclude any individual substituents, structures, or groups thereof, or any members of a claimed group, less than the full measure of this disclosure can be claimed for any reason. Throughout this disclosure, various patents, patent applications and publications are referenced. The disclosures of these patents, patent applications and publications are incorporated into this disclosure by reference in their entireties in order to more fully describe the state of the art as known to those skilled therein as of the date of this disclosure. This disclosure will govern in the instance that there is any inconsistency between the patents, patent applications and publications cited and this disclosure.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention.

The traditional Chinese herbal composition provided by the present disclosure may be prepared from raw materials comprising about 30 parts by weight of the Ziziphi Spinosae Semen. The present disclosure has no particular limitation on the source of the Ziziphi Spinosae Semen, and a product prepared by conventional processing method or a conventionally commercial product may be used. In the present disclosure, the Ziziphi Spinosae Semen has actions of nourishing the heart and quieting the spirit, conciliating five internal organs.

The traditional Chinese herbal composition provided by the present disclosure may be prepared from raw materials comprising about 20-30 parts by weight, preferably about 22-28 parts by weight, and more preferably about 25 parts by weight of the Rehmanniae Radix. The present disclosure has no particular limitation on the source of the Rehmanniae Radix, and a conventionally commercial product may be used. In the present disclosure, the Rehmanniae Radix has action of nourishing yin and engendering liquid.

The traditional Chinese herbal composition provided by the present disclosure may be prepared from raw materials comprising about 20-30 parts by weight, preferably about 22-28 parts by weight, and more preferably about 25 parts by weight of the Trichosanthis Radix. The present disclosure has no particular limitation on the source of the Trichosanthis Radix, and a conventionally commercial product may be used. In the present disclosure, the Trichosanthis Radix has action of engendering liquid and dispersing swelling.

The traditional Chinese herbal composition provided by the present disclosure may be prepared from raw materials comprising about 40-50 parts by weight, preferably about 42-48 parts by weight, and more preferably about 45 parts by weight of the Paeoniae Radix Alba. The present disclosure has no particular limitation on the source of the Paeoniae Radix Alba, and a conventionally commercial product may be used. In the present disclosure, the Paeoniae Radix Alba has actions of calming the liver and relieving pain, nourishing the blood and regulating menstruation, and retaining yin with astringent and checking sweating.

The traditional Chinese herbal composition provided by the present disclosure may be prepared from raw materials comprising about 30 parts by weight of the Coicis Semen Preparata. The present disclosure has no particular limitation on the source of the Coicis Semen Preparata, and a product prepared by conventional processing method or a conventionally commercial product may be used. In the present disclosure, the Coicis Semen Preparata has actions of disinhibiting water and fortifying the spleen.

The traditional Chinese herbal composition provided by the present disclosure may be prepared from raw materials comprising about 20 parts by weight of the Ginseng Radix et Rhizoma. The present disclosure has no particular limitation on the source of the Ginseng Radix et Rhizoma, and a conventionally commercial product may be used. In the present disclosure, the Ginseng Radix et Rhizoma has an action of powerfully reinforcing original qi.

The traditional Chinese herbal composition provided by the present disclosure may be prepared from raw materials comprising about 10 parts by weight of the Olibanum. The present disclosure has no particular limitation on the source of the Olibanum, and a conventionally commercial product may be used. In the present disclosure, the Olibanum has actions of promoting blood circulation to arrest pain, dispersing swelling and engendering flesh.

The traditional Chinese herbal composition provided by the present disclosure may be prepared from raw materials comprising about 10 parts by weight of the Myrrha. The present disclosure has no particular limitation on the source of the Myrrha, and a conventionally commercial product may be used. In the present disclosure, the Myrrha has actions of promoting blood circulation to arrest pain, dispersing swelling and engendering flesh.

The traditional Chinese herbal composition provided by the present disclosure may be prepared from raw materials comprising about 20-30 parts by weight, preferably about 22-28 parts by weight, and more preferably about 25 parts by weight of the Testudinis Carapax et Plastrum Preparata Cum Aceto. The present disclosure has no particular limitation on the source of the Testudinis Carapax et Plastrum Preparata Cum Aceto, and a product prepared by conventional processing methods or a conventionally commercial product may be used. In the present disclosure, the Testudinis Carapax et Plastrum Preparata Cum Aceto has actions of nourishing yin and suppressing yang, nourishing blood, and tonifying the heart.

The traditional Chinese herbal composition provided by the present disclosure may be prepared from raw materials comprising about 20-30 parts by weight, preferably about 22-28 parts by weight, and more preferably 25 parts by weight of the Trionycis Carapax Preparata Cum Aceto. The present disclosure has no particular limitation on the source of the Trionycis Carapax Preparata Cum Aceto, and a product prepared by conventional processing method or a conventionally commercial product may be used. In the present disclosure, the Trionycis Carapax Preparata Cum Aceto has actions of nourishing yin and suppressing yang, and softening hardness to dissipate stagnation.

The traditional Chinese herbal composition provided by the present disclosure may be prepared from raw materials comprising about 30 parts by weight of the Agrimoniae Herba. The present disclosure has no particular limitation on the source of the Agrimoniae Herba, and a conventionally commercial product may be used. In the present disclosure, the Agrimoniae Herba has an action of dispersing accumulations.

The traditional Chinese herbal composition provided by the present disclosure may be prepared from raw materials comprising about 10-20 parts by weight, preferably about 12-18 parts by weight, and more preferably about 15 parts by weight of the Alpiniae Oxyphyllae Fructus. The present disclosure has no particular limitation on the source of the Alpiniae Oxyphyllae Fructus, and a conventionally commercial product may be used. In the present disclosure, the Alpiniae Oxyphyllae Fructus has actions of inducing tranquilization and sharpening the wits.

The traditional Chinese herbal composition provided by the present disclosure may be prepared from raw materials comprising about 5 parts by weight of the Toosendan Fructus. The present disclosure has no particular limitation on the source of the Toosendan Fructus, and a conventionally commercial product may be used. In the present disclosure, the Toosendan Fructus has actions of moving qi and arresting pain.

The traditional Chinese herbal composition provided by the present disclosure may be prepared from raw materials comprising about 20 parts by weight of the Poria. The present disclosure has no particular limitation on the source of the Poria, and a conventionally commercial product may be used. In the present disclosure, the Poria has actions of quieting the heart, inducing tranquilization, and tonifying the heart and the spleen.

The traditional Chinese herbal composition provided by the present disclosure may be prepared from raw materials comprising about 10 parts by weight of the Platycodonis Radix. The present disclosure has no particular limitation on the source of the Platycodonis Radix, and a conventionally commercial product may be used. In the present disclosure, the Platycodonis Radix has actions of diffusing the lungs and dispersing welling-abscesses.

The traditional Chinese herbal composition provided by the present disclosure may be prepared from raw materials comprising 10 parts by weight of the Polygalae Radix. The present disclosure has no particular limitation on the source of the Polygalae Radix, and a conventionally commercial product may be used. In the present disclosure, the Polygalae Radix has actions of inducing tranquilization and sharpening the wits.

Step 1, soaking the Ziziphi Spinosae Semen, the Rehmanniae Radix, the Trichosanthis Radix, the Paeoniae Radix Alba, the Coicis Semen Preparata, the Ginseng Radix et Rhizoma, the Olibanum, the Myrrha, the Testudinis Carapax et Plastrum Preparata Cum Aceto, the Trionycis Carapax Preparata Cum Aceto, the Agrimoniae Herba, the Alpiniae Oxyphyllae Fructus, the Toosendan Fructus, the Poria, the Platycodonis Radix, and the Polygalae Radix in water;

Step 2, conducting a first decoction on medicinal materials soaked in step 1 to obtain a first decoction and first dregs;

Step 3, mixing the first dregs obtained in step 2 with water for a second decoction to obtain a second decoction and second dregs;

Step 4, mixing the second dregs obtained in step 3 with water for a third decoction to obtain a third decoction and third dregs; and Step 5, mixing the decoctions obtained in steps 2, 3, and 4 to obtain the traditional Chinese herbal composition.

In the present disclosure, the Ziziphi Spinosae Semen, the Rehmanniae Radix, the Trichosanthis Radix, the Paeoniae Radix Alba, the Coicis Semen Preparata, the Ginseng Radix et Rhizoma, the Olibanum, the Myrrha, the Testudinis Carapax et Plastrum Preparata Cum Aceto, the Trionycis Carapax Preparata Cum Aceto, the Agrimoniae Herba, the Alpiniae Oxyphyllae Fructus, the Toosendan Fructus, the Poria, the Platycodonis Radix, and the Polygalae Radix are soaked in water. In the present disclosure, the foregoing medicinal materials may preferably be compacted before soaking; an amount of the water in the soaking may preferably be about 2-3 cm above the medicinal materials; the soaking may preferably be conducted for about 15-25 min, and more preferably about 20 min.

In the present disclosure, a first decoction is conducted on the medicinal materials after the soaking to obtain a first decoction and first dregs. In the present disclosure, the decoction may preferably be implemented by boiling a liquor and decocting the liquor; the decocting may last for about 20-40 min, and more preferably about 30 min.

In the present disclosure, the first dregs obtained are mixed with water for a second decoction to obtain a second decoction and second dregs. In the disclosure, an amount of the water may preferably be about 2-3 cm above the first dregs. In the present disclosure, the decoction may preferably be implemented by boiling a liquor and decocting the liquor; the decocting may last for about 20-40 min, and more preferably about 30 min.

In the present disclosure, the second dregs obtained are mixed with water for a third decoction to obtain a third decoction and third dregs. In the disclosure, an amount of the water may preferably be about 2-3 cm above the second dregs. In the present disclosure, the decoction may preferably be implemented by boiling a liquor and decocting the liquor; the decocting may preferably last about 15-25 min, and more preferably about 20 min.

In the present disclosure, the decoctions obtained separately are mixed to obtain the traditional Chinese herbal composition. The present disclosure has no particular limitation on the method for the mixing, and a conventional mixing method may be used.

The present disclosure further provides a honeyed pill for treating pulmonary nodules, including the raw materials of the traditional Chinese herbal composition according to the above solution and honey. In the present disclosure, the raw materials of the traditional Chinese herbal composition and the honey may be in a mass ratio of 1:(1.2-1.5). The present disclosure has no particular limitation on the source of the honey, and a conventionally commercial product may be used.

In the present disclosure, a preparation method of the honeyed pill may preferably include steps of: powdering, honey preparation, honey refining, blending, and pill rolling.

In the present disclosure, the powdering refers to drying and making the Ziziphi Spinosae Semen, the Rehmanniae Radix, the Trichosanthis Radix, the Paeoniae Radix Alba, the Coicis Semen Preparata, the Ginseng Radix et Rhizoma, the Olibanum, the Myrrha, the Testudinis Carapax et Plastrum Preparata Cum Aceto, the Trionycis Carapax Preparata Cum Aceto, the Agrimoniae Herba, the Alpiniae Oxyphyllae Fructus, the Toosendan Fructus, the Poria, the Platycodonis Radix, and the Polygalae Radix into fine powders. The present disclosure has no particular limitation on the method for the drying, and baking or sun-drying may preferably be used. The present disclosure has no particular limitation on the method for making into fine powders, and a pulverizer may preferably be used for making into fine powders.

In the present disclosure, the honey preparation refers to preparing the honey in a ratio of the total mass of the traditional Chinese herbal composition to the mass of the honey of 1:(1.2-1.5).

In the present disclosure, the honey refining refers to cooking the honey. In honey refining, the honey is boiled and slowly cooked. In the present disclosure, when yellow froths are found to float on the honey, a drop of honey is dipped with a bamboo chopstick, and the bamboo chopstick is transferred over a bowl with cold water to drop the honey into the water; if the honey is not diffuse but sinks to the bottom (namely "droplets into beads in water"), the honey will be well-cooked.

In the present disclosure, the blending follows the following steps: spooning the well-cooked honey to pour into a sterile basin with medical powder, stirring the honey in the medical powder with thick bamboo chopsticks, pouring the honey while blending the medical powder, and stopping adding the honey until dry medical powder is almost invisible. In the present disclosure, the pill rolling may be implemented by a conventional pill rolling method. In the present disclosure, during the pill rolling, a small amount of glycerol, sesame oil, or peanut oil may be applied in the palm before the pill rolling.

In the present disclosure, a well-prepared honeyed pill is further subjected to packaging and storage. Preferably, the well-prepared honeyed pill has a round and smooth shape and a dense and moist surface, without visible fiber or other color stains. After the pill sweats and the surface hardens, the pill is packaged with wax paper, cellophane, plastic bag, or bee-waxed shell and stored in a cool and dry place. In the present disclosure, the pill may preferably sweat for about 2-5 days, and more preferably about 3 days.

The present disclosure has no particular limitation on pharmaceutical dosage forms of the traditional Chinese herbal composition, preferably including a tablet, a granule, a capsule, and an oral liquid preparation. The present disclosure has no particular limitation on excipients for the pharmaceutical dosage forms, as long as excipients corresponding to conventional preparation of the tablet, the granule, the capsule, and the oral liquid preparation may be used.

Also disclosed herein are methods of treating pulmonary nodules, the method comprising administering to a subject, the traditional Chinese herbal composition described herein. In the present disclosure, the traditional Chinese herbal composition may preferably be administered orally; a dosage of the traditional Chinese herbal composition may preferably be about 100-200 mL/time, and more preferably about 100 mL/time, twice a day.

Also disclosed herein are methods of treating pulmonary nodules, the method comprising administering to a subject, the honeyed pill described herein. In the present disclosure, the honeyed pill may preferably be administered orally; a dosage of the honeyed pill may preferably be about 9 g/pill; the honeyed pill may preferably be administered twice a day.

In the present disclosure, the traditional Chinese herbal composition and the honeyed pill may preferably be administered once about half an hour before and after meals, respectively.

The technical solutions of the present disclosure will further be described in detail with reference to specific examples. The technical solutions of the present disclosure include, but are not limited to, the following examples. The following are provided for exemplification purposes only and are not intended to limit the scope of the embodiments described in broad terms above.

Example 1

A preparation method of a traditional Chinese herbal composition for treating pulmonary nodules followed the following steps:

Step 1, 30 g of Ziziphi Spinosae Semen, 30 g of Rehmanniae Radix, 30 g of Trichosanthis Radix, 30 g of Coicis Semen Preparata, 50 g of Paeoniae Radix Alba, 20 g of Ginseng Radix et Rhizoma, 10 g of Olibanum, 10 g of Myrrha, 30 g of Agrimoniae Herba, 30 g of Testudinis Carapax et Plastrum Preparata Cum Aceto, 30 g of Trionycis Carapax Preparata Cum Aceto, 20 g of Alpiniae Oxyphyllae Fructus, 5 g of Toosendan Fructus, 20 g of Poria, 10 g of Platycodonis Radix, and 10 g of Polygalae Radix were compacted, immersed with water 2 cm above the surface of the medicinal materials, and soaked for 20 min;

Step 2, a liquor of the soaked medicinal materials were boiled and decocted for 30 min to obtain a first decoction and first dregs;

Step 3, the first dregs obtained were mixed and immersed with water 2 cm above the surface, and a resulting liquor was boiled and decocted for 30 min to obtain a second decoction and second dregs;

Step 4, the second dregs obtained were mixed and immersed with water 2 cm above the surface, and a resulting liquor was boiled and decocted for 20 min to obtain a third decoction and third dregs; and Step 5, the decoctions obtained in steps 2, 3, and 4 were mixed to obtain the traditional Chinese herbal composition.

Example 2

A preparation method of a honeyed pill for treating pulmonary nodules followed the following steps:

Step 1, 30 g of Ziziphi Spinosae Semen, 30 g of Rehmanniae Radix, 30 g of Trichosanthis Radix, 30 g of Coicis Semen Preparata, 50 g of Paeoniae Radix Alba, 20 g of Ginseng Radix et Rhizoma, 10 g of Olibanum, 10 g of Myrrha, 30 g of Agrimoniae Herba, 30 g of Testudinis Carapax et Plastrum Preparata Cum Aceto, 30 g of Trionycis Carapax Preparata Cum Aceto, 20 g of Alpiniae Oxyphyllae Fructus, 5 g of Toosendan Fructus, 20 g of Poria, 10 g of Platycodonis Radix, and 10 g of Polygalae Radix were sun-dried and pulverized into fine powders in a pulverizer;

Step 2, according to 245 g of the foregoing medicinal powders, 294 g of honey was prepared in a ratio of 1:1.2;

Step 3, the honey was cooked; when refining the honey, the honey was boiled and cooked; when yellow froths were found to float on the honey, a drop of honey was dipped with a bamboo chopstick, and the bamboo chopstick was transferred over a bowl with cold water to drop the honey into the water; if the honey was not diffuse but sank to the bottom (namely "droplets into beads in water"), the honey was well-cooked;

Step 4, the well-cooked honey was spooned to pour into a sterile basin with medical powder and stirred in the medical powder with thick bamboo chopsticks, the honey was poured while blending the medical powder, and addition of the honey was stopped until dry medical powder was almost invisible;

Step 5, during the pill rolling, a small amount of glycerol was applied in the palm, and each pill weighed 9 g; and Step 6, a well-prepared honeyed pill had a round and smooth shape and a dense and moist surface, without visible fiber or other color stains; after the pill sweat (for 3 days) and the surface hardened, the pill was packaged with wax paper, cellophane, plastic bag, or bee-waxed shell and stored in a cool and dry place.

Example 3

Mrs. Zhao, female, 58-year-old, came for a first visit. Chief complaint (CC): Recurrent cough and shortness of breath for six months. History of present illness (HPI): The patient suffered from cough, shortness of breath, and chest distress under no obvious predisposing causes six months ago. She took cold medicine and antitussive and phlegm-resolving drugs herself, but symptoms were recurrent. On lung CT scan, multiple nodules were visible in the lungs, with a maximum diameter of 3.8×2.3 cm, but they were untreated. At present, she coughed and expectorated a small amount of viscous sputum; she had hasty panting, shortness of breath, and chest distress on exertion; she palpitated occasionally; she had frequent sighing and dry mouth. Both appetite and sleep were fair. Urination and defecation were normal. Tongue and pulse: The tongue was enlarged and dark red; the tongue fur was yellow and greasy; the pulse was stringy, fine and rapid, weak at either Chi pulse.

TCM diagnosis: lung accumulation (due to the insufficiency of liver yin and the accumulation and binding of both phlegm and stasis); Western medical diagnosis: pulmonary nodules.

The patient was given 10 doses of the traditional Chinese herbal composition prepared in Example 1; each dose was decocted with water to obtain 300 mL of decoction, and the patient took 150 mL orally each time, twice a day.

The patient was reviewed about 4 months later. Symptoms: she occasionally coughed and expectorated a small amount of viscous sputum; she had reduced hasty panting on exertion and shortness of breath, and chest distress was relieved; both appetite and sleep were fair; urination and defecation were normal. Tongue and pulse: The tongue was enlarged and dark red; the tongue fur was white and slightly greasy; the pulse was stringy and fine. Lung CT scan was reviewed, and revealed that multiple nodules were visible in the lungs, with a maximum diameter of 0.6×0.5 cm. After administration of the traditional Chinese herbal composition provided by the present disclosure, pulmonary nodules were reduced significantly.

Example 4

Mrs. Bai, female, 72-year-old, came for a first visit. CC: Intermittent fever for two months and pulmonary nodules found for one month. HPI: The patient was admitted to Songyuan Oilfields General Hospital due to left nephritis caused by urinary tract infection. Lung CT scan revealed pulmonary masses, with the longest diameter of about 1.5 cm, with bilateral pleural effusions. She was treated by intravenous drip of antibiotics (unknown). She was discharged from the hospital as symptoms were slightly relieved. She developed a fever again two weeks after discharge, and the highest body temperature was 38.6° C. Then, she came for a visit to our clinic. At present, she complained of fever, cough (mainly dry cough), fatigue, shortness of breath, occasional chest distress, and palpitation; she had a poor appetite; she slept poorly and lightly; she passed less urine and had difficult urination; she had a bowel movement at an interval of 1-2 days, and the stools were dry.

TCM diagnosis: lung accumulation and fever due to internal injury (due to the insufficiency of liver yin and the accumulation and binding of both phlegm and stasis); Western medical diagnosis: pulmonary nodules with pleural effusions.

The patient was given 10 doses of the traditional Chinese herbal composition prepared in Example 1; each dose was decocted with water to obtain 300 mL of decoction, and the patient took 150 mL orally each time, twice a day.

She was reviewed about 5 months later. Symptoms: all symptoms were relieved; both appetite and sleep were fair; urination and defecation were fair; lung CT scan was reviewed, and revealed that no pulmonary nodule was seen and pleural effusions vanished.

Example 5

A clinical experiment of the treatment of pulmonary nodules with the present disclosure and the result analysis 1 Materials and Methods 1.1 Subjects Subjects were selected from 33 patients with pulmonary nodules (17 males and 16 females; aged 43-89 years; mean age: 64.5 years) admitted to the Affiliated Hospital of Changchun University of Chinese Medicine over a period of about 1 year.

1.2 Diagnostic Criteria for Pulmonary Nodules 1.2.1 Diagnostic Criteria in Western Medicine Pulmonary nodules refer to well-circumscribed, opaque, solitary or multiple nodules with a diameter of ≤3 cm and surrounded by aerated lung tissues, without pulmonary atelectasis, hilar lymphadenophathy, and pleural effusion.

1.3 Screening Criteria

Inclusion Criteria:

1. Lung CT signs revealed small nodules, nodular densities, or focal pulmonary linear densities; alternatively, there were the above signs on lung CT scan before lung surgery.
2. Patients or their relatives agreed to receive TCM treatment.
3. Related diseases that had possible effects on measurements were ruled out, for example, pulmonary infection and interstitial lung disease.

Exclusion Criteria:

1. Lung CT scan findings of a patient, combined with other manifestations of diseases, could not be determined as micronodules, small nodules, pulmonary nodules and neoplasms.
2. A patient needed to receive lung CT scan before treatment and needed a regular review of lung CT scan after treatment, with at least one review.

1.4 Method

The patients were given 10 doses of the traditional Chinese herbal composition prepared in Example 1; each dose was decocted with water to obtain 300 mL of decoction, and the patients took 150 mL orally each time, twice a day. Their pre- and post-treatment efficacy was compared 4 weeks after oral administration.

1.5 Response Criteria:

I. Symptom Observation:

Observation was made on the improvement of clinical symptoms of patients by TCM treatment, such as cough, expectoration, chest distress, shortness of breath, fatigue, and inappetence.

Outcome measures: Symptoms of TCM were divided into four grades according to clinical observations:

(0) Asymptomatic
(1) Mild
(2) Moderate
(3) Severe

Treatment conditions were recorded according to the occurrence of symptoms.

Evaluation method: Comparison of total scores of pre- and post-treatment symptoms (before/after treatment)

Effectual: Symptoms disappear, or symptom scores decrease by ≥⅔

Effective: Symptoms are relieved, or symptom scores decrease by ≥⅓ but ≤⅔

Ineffective: Symptoms are not relieved, or symptom scores decrease by ≤⅓

II. Imaging Findings:

Refer to the Response Evaluation Criteria in Solid Tumors (RECIST) 2009

1. CR: In the observation period, all lesions disappear, and this condition lasts for at least 4 weeks.
2. PR: In the observation period, among all lesions, the long diameter of the largest one is reduced by at least 30%, and this condition lasts for at least 4 weeks.
3. PD: In the observation period, the long diameter of the largest lesion is increased by 20%, the lesion is increased by at least 5 mm, or new lesions appear.
4. SD: In the observation period, the lesion meets neither PR nor PD.

NOTE*Calculation results are determined according to the maximum long diameter of the lesion.

1.6 Result Analysis

TABLE 1

| | | Results of TCM symptom scores | | | |
| --- | --- | --- | --- | --- | --- |
| Group | Enrollment | Effectual | Effective | Ineffective | Overall response rate (%) |
| Oral administration of the traditional Chinese herbal composition in Example 1 | 33 | 10 | 17 | 6 | 81.8 |

TABLE 2

| Analysis of imaging findings | | | | | |
|---|---|---|---|---|---|
| Group | Enrollment | CR | PR | SD | PD | Response rate (%) |
| Oral administration of the traditional Chinese herbal composition in Example 1 | 33 | 5 | 15 | 10 | 3 | 60.6 |

It can be seen from the above examples that administration of the traditional Chinese herbal composition provided by the present disclosure can effectively improve the symptom of pulmonary nodules and remit the progression of pulmonary nodule lesions.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A traditional Chinese herbal composition for treating pulmonary nodules, prepared from raw materials comprising the following in relative parts by weight:

30 parts by weight of Ziziphi Spinosae Semen, 20-30 parts by weight of Rehmanniae Radix, 30 parts by weight of Trichosanthis Radix, 40-50 parts by weight of Paeoniae Radix Alba, 30 parts by weight of Coicis Semen Preparata, 20 parts by weight of Ginseng Radix et Rhizoma, 10 parts by weight of Olibanum, 10 parts by weight of Myrrha, 20-30 parts by weight of Testudinis Carapax et Plastrum Preparata Cum Aceto, 20-30 parts by weight of Trionycis Carapax Preparata Cum Aceto, 30 parts by weight of Agrimoniae Herba, 10-20 parts by weight of Alpiniae Oxyphyllae Fructus, 5 parts by weight of Toosendan Fructus, 20 parts by weight of Poria, 10 parts by weight of Platycodonis Radix, and 10 parts by weight of Polygalae Radix.

2. The traditional Chinese herbal composition according to claim 1, wherein the traditional Chinese herbal composition is in the pharmaceutical dosage form of a tablet, a granule, a capsule, or an oral liquid preparation.

3. A honeyed pill for treating pulmonary nodules, comprising the traditional Chinese herbal composition according to claim 1 and honey, wherein a total mass of raw materials of the traditional Chinese herbal composition and a mass of the honey are in a ratio of 1:(1.2-1.5).

4. A preparation method of the traditional Chinese herbal composition according to claim 1, comprising the following steps:

step 1, soaking the Ziziphi Spinosae Semen, the Rehmanniae Radix, the Trichosanthis Radix, the Paeoniae Radix Alba, the Coicis Semen Preparata, the Ginseng Radix et Rhizoma, the Olibanum, the Myrrha, the Testudinis Carapax et Plastrum Preparata Cum Aceto, the Trionycis Carapax Preparata Cum Aceto, the Agrimoniae Herba, the Alpiniae Oxyphyllae Fructus, the Toosendan Fructus, the Poria, the Platycodonis Radix, and the Polygalae Radix in water;

step 2, conducting a first decoction on medicinal materials soaked in step 1 to obtain a first decoction and first dregs;

step 3, mixing the first dregs obtained in step 2 with water for a second decoction to obtain a second decoction and second dregs;

step 4, mixing the second dregs obtained in step 3 with water for a third decoction to obtain a third decoction and third dregs; and step 5, mixing the decoctions obtained in steps 2, 3, and 4 to obtain the traditional Chinese herbal composition.

5. The preparation method according to claim 4, wherein the soaking in step 1 is conducted for about 15-25 min.

6. The preparation method according to claim 4, wherein an amount of the water in step 1, 3, or 4 is each independently about 2-3 cm above the surface of the medicinal materials, that of the first dregs, or that of the second dregs.

7. The preparation method according to claim 4, wherein the first decoction, the second decoction, and the third decoction are each independently implemented by boiling a liquor and decocting the liquor.

8. The preparation method according to claim 7, wherein the decocting each independently lasts for about 20-40 min during the first decoction and the second decoction.

9. The preparation method according to claim 7, wherein the decocting lasts for about 15-25 min during the third decoction.

* * * * *